(12) United States Patent
Popp

(10) Patent No.: US 9,138,451 B2
(45) Date of Patent: Sep. 22, 2015

(54) PLANT EXTRACT HYDROLYSATES AND ANTIBACTERIAL PRODUCT CONTAINING THE SAME

(75) Inventor: Michael A. Popp, Lauf (DE)

(73) Assignee: Bionorica SE, Neumarkt (DE)

( * ) Notice: Subject to any disclaimer, the term of this patent is extended or adjusted under 35 U.S.C. 154(b) by 99 days.

(21) Appl. No.: 13/126,797

(22) PCT Filed: Nov. 2, 2009

(86) PCT No.: PCT/EP2009/064477
§ 371 (c)(1),
(2), (4) Date: May 6, 2011

(87) PCT Pub. No.: WO2010/049542
PCT Pub. Date: May 6, 2010

(65) Prior Publication Data
US 2011/0244041 A1 Oct. 6, 2011

(30) Foreign Application Priority Data

Oct. 31, 2008 (DE) .......................... 10 2008 054 127
Mar. 5, 2009 (DE) .......................... 10 2009 011 152

(51) Int. Cl.
*A61K 36/00* (2006.01)
*A61K 36/53* (2006.01)
*A61K 36/11* (2006.01)

(52) U.S. Cl.
CPC ................. *A61K 36/53* (2013.01); *A61K 36/11* (2013.01)

(58) Field of Classification Search
None
See application file for complete search history.

(56) References Cited

U.S. PATENT DOCUMENTS

| | | | | |
|---|---|---|---|---|
| 3,449,328 | A * | 6/1969 | Hardman | ......................... 540/18 |
| 2003/0211077 | A1 | 11/2003 | An et al. | |
| 2004/0033278 | A1 | 2/2004 | Lu | |
| 2006/0057236 | A1 * | 3/2006 | Runkel et al. | ................. 424/774 |

FOREIGN PATENT DOCUMENTS

| | | | |
|---|---|---|---|
| JP | 09078061 | A * | 3/1997 |
| WO | 99/33480 | A | 7/1999 |
| WO | 02/02607 | A2 | 1/2002 |

OTHER PUBLICATIONS

Mansouri et al, An ontogenetic study on the sapogenin contents of ivy, Pharmazie 50, 50 (9): 642-3.*
Krolicka et al: "Stimulation of antibacterial naphthoquinones and flavonoids accumulation in carnivorous plants grown in vitro by addition of elicitors" Enzyme and Microbial Technology, Stoneham, MA, US, vol. 42, No. 3, Jan. 15, 2008, pp. 216-221, XP022422532 ISSN: 0141-0229; Invention 1; p. 216, col. 1, line 1—p. 217, col. 1, line 15; p. 217, col. 2, paragraph 7; p. 218, col. 1, paragraph 3; p. 219, col. 1, line 1—col. 2, line 12; table 1.
Ani V et al: "Antioxidant and antibacterial activities of polyphenolic compounds from bitter cumin (*Cuminum nigrum* L.)" European Food Research and Technology ; Zeitschrift Für Lebensmitteluntersuchung Und—Forschung A, Springer, Berlin, DE, vol. 224, No. 1, Mar. 9, 2006, pp. 109-115, XP019441218; ISSN: 1438-2385; Invention 1; p. 110, col. 1, paragraph 3; p. 114, col. 1, paragraph 2—p. 115, col. 1, line 2; table 4.
Beckmann S. and Geiger H.: "Über Zwei Kaempferolglykoside Des Sumpfschachtelhalms (*Equisetum palustre*)" Phytochemistry, vol. 2, 1963, pp. 281-287, XP002570479 Invention 1; p. 284, line 20-line 46; p. 286, line 21-line 30.
[Online] Nov. 6, 2006, XP002570480 Retrieved from the Internet: URL:http://www.news-ticker.ch/pm.php?news_id=4762461 &aktion=nf> [retrieved on Feb. 25, 2010].
Joksic Gordana et al: "Antibacterial medicinal plants *Equiseti* herba and *Ononidis* radix modulate micronucleus formation in human lymphocytes in vitro." Journal of Environmental Pathology Toxicology and Oncology, vol. 22, No. 1, 2003, pp. 41-48, XP002570821 ISSN: 0731-8898.
Schier W: "*Equisetum arvense* as medicinal plant" Zeitschrift Fur Phytotherapie 1985 DE, vol. 6, No. 4, 1985, pp. 126-128, XP002570822 ISSN: 0722-348X.
Do Monte Fabricio Hoffmann Martins et al: "Antinociceptive and anti-inflammatory properties of the hydroalcoholic extract of stems from *Equisetum arvense* L. in mice" Pharmacological Research, Academic Press, London, GB, vol. 49, No. 3, Mar. 1, 2004, pp. 239-243, XP009126388 ISSN: 1043-6618, [retrieved on Dec. 2, 2003].
Chen G-H et al: "Progress in pharmacological effects of compositions of *Astragalus membranaceus*" Zhongguo Xin Yao Zazhi—Chinese New Drugs Journal, Gai—Kan Bianjibu, Beijing, CN, vol. 17, No. 17, Jan. 1, 2008, pp. 1482-1485, XP008126582 ISSN: 1003-3734, Invention 13.
Mikamo Hiroshige et al: "Effects of crude herbal ingredients on intrauterine infection in a rat model" Current Therapeutic Research, vol. 59, No. 2, Feb. 1998, pp. 122-127, XP002601354 ISSN: 0011-393X.

* cited by examiner

*Primary Examiner* — Qiuwen Mi
(74) *Attorney, Agent, or Firm* — Drinker Biddle & Reath LLP

(57) ABSTRACT

The invention relates to a hydrolyzate from at least one extract of at least one plant material selected from the group consisting of at least one genus: *Equiseti, Juglandis, Millefolii, Quercus, Taraxaci, Althaeae, Matricariae, Centaurium, Levisticum, Rosmarinus, Angelica(e), Artemisia, Astragalus, Leonurus, Salvia, Saposhnikovia, Scutellaria, Siegesbeckia, Armoracia, Capsicum, Cistus, Echinacea, Echinacea, Galphimia, Hedera, Melia, Olea, Pelargonium, Phytolacca, Primula, Salix, Thymus, Vitex*, and *Vitis*; and to a mixture thereof and to a method of production and the use thereof. The invention further relates to an agent and drug obtainable on the basis of the hydrolyzate.

22 Claims, No Drawings

PLANT EXTRACT HYDROLYSATES AND ANTIBACTERIAL PRODUCT CONTAINING THE SAME

The invention relates to a hydrolyzate comprising at least one extract of at least one plant material selected from the respective geni, in particular the species of *Equiseti herba* (horsetail herb), *Juglandis folium* (walnut leaf), *Millefolii herba* (yarrow), *Quercus cortex* (oak bark), *Taraxaci herba* (dandelion herb), *Althaeae, radix* (marshmallow root), and *Matricariae flos* (or *Flos chamomillae* (chamomile flower)), *Centaurium erythraea* (centaury), *Levisticum officinale* (lovage), *Rosmarinus officinalis* (rosemary), *Angelica dahurica* (Dahurican *angelica* root, Pinyin name: Bai Zhi), *Angelica sinensis* (Chinese *angelica*, Pinyin name: Dong quai), *Artemisia scoparia* (redstem wormwood, Pinyin name: Yin-chen), *Astragalus membranaceus* (var. *Mongolicus*) (Chinese milkvetch, Chin.: Huang Qi), *Leonurus japonicus* (Chinese motherwort, Chin.: Yimucao), *Salvia miltiorrhiza* (red sage, Chin.: Danshen), *Saposhnikovia divaricata* (siler, PinYin name: Fang-feng), *Scutellaria baicalensis* (Baikal skullcap, Banzhilian), *Siegesbeckia pubescens* (*Siegesbeckia* herb, Pinyin name: Xi Xian Cao), *Armoracia rusticana* (horseradish), *Capsicum* sp. (peppers), *Cistus incanus* (hairy rockrose), *Echinacea angustifolia* (blacksamson echinacea), *Echinacea purpurea* (purple coneflower), *Galphimia glauca*, *Hedera helix* (English ivy), *Melia toosendan* (chinaberry fruit, Chin.: Chuan Lian Zi), *Olea europaea* (olive), *Pelargonium* sp. (geranium), *Phytolacca americana* (American pokeweed), *Primula veris* (cowslip), *Salix* sp. (willow), *Thymus* L. (thyme), *Vitex agnus castus* (lilac chastetree), and *Vitis vinifera* (common grape vine) or a mixture thereof, and to a method for producing the same and to the use thereof. The invention further relates to an antibacterial agent and pharmaceutical product that can be obtained therefrom.

Imupret® (registered trademark of BIONORICA AG), is a known mixture made of plant drugs, which is produced from *Equiseti herba* (horsetail herb), *Juglandis folium* (walnut leaf), *Millefolii herba* (yarrow), *Quercus cortex* (oak bark), *Taraxaci herba* (dandelion herb), *Althaeae radix* (marshmallow root) and *Matricariae flos* (or *Flos chamomillae* (chamomile flower)). By combining these seven medicinal plants, a compound is obtained, which can be used to achieve sufficient effect for medicinal purposes. This compound is particularly suited for treating respiratory tract infections, notably recurrent and chronic respiratory infections, preferably tonsillitis. Tonsillitis or sore throat, (tonsillo)pharyngitis, or throat infection, is an inflammation of the lymphoepithelial tissues of the lympathic pharyngeal space, notably the palatine tonsils. A differentiation is made between a.) acute tonsillitis, which is typically caused by viruses (approximately 80%; adenoviruses, parainfluenza viruses) and group A beta-hemolytic streptococci, and less frequently by staphylococci and pneumococci. The inflammation is typically marked by high fever, a sore throat, muffled speech, tenderness to touch and swelling of the submandibular lymph nodes, with reddening and swelling of the tonsils (angina catarrhalis), frequently isolated spots on the tonsils (referred to as patches) at the tonsillar crypt openings (angina lacunaris), or via lymph follicles (angina follicularis, pneumococci angina); and b) chronic tonsillitis, which is typically caused by a mixed infection of anaerobic and aerobic pathogens, with the involvement of group A beta-hemolytic streptococci (actually new infections caused by different serotypes); pathological anatomical retention of cell detritus, tonsillar crypt abscesses, fibrosing and necrosis of the parenchyma; involvement of the peritonsillar tissue; sore throat; minor discomfort (so-called scratchy throat), enlarged submandibular lymph nodes, halitosis, reddened tonsils with a scarred and bumpy surface, peritonsillar tenderness to pressure, discharge of pus when pressing the spatula on the front palatal arch, and cell detritus on the tonsillar crypts.

Canephron® (registered trademark of BIONORICA AG) is a known mixture of three plant drugs, which is to say *Centaurium etythraea* (centaury), *Levisticum officinale* (lovage; powder made of lovage root), *Rosmarinus officinalis* (rosemary; powder made of rosemary leaves), which is produced from these plant materials. By combining these three medicinal plants, a compound is obtained, which can be used to achieve sufficient effect for medicinal purposes. This compound is particularly suited for treating urinary tract infections and has an anti-inflammatory effect on the urinary tract.

Moreover, Bronchipret® (registered trademark of BIONORICA AG) made of thyme (*Thymus* L.) combined with cowslip (*Primula veris*) or English ivy (*Hedera helix*) is known for its antibacterial effect.

The respective ground raw drugs and ethanolic-aqueous extracts or dry extracts produced therefrom (which can be produced, for example, by withdrawing the solvent or extracting agent at reduced pressure) of the plants mentioned above have been successfully applied due to the exclusive plant-based healing power thereof. The medicinal plants used in Bronchipret®, Canephron® or Imupret® are carefully selected, analyzed, and processed. BIONORICA achieves the consistent quality of the pharmaceutical product by employing optimally developed cultivation and harvesting strategies and extremely stringent quality control. Each individual drug contributes a part to the unique efficacy of the compound.

*Angelica dahurica, Angelica sinensis, Artemisia scoparia, Astragalus membranaceus* (var. *mongolicus*), *Leonurus japonicus, Salvia miltiorrhiza, Saposhnikovia divaricata, Scutellaria baicalensis* and *Siegesbeckia pubescens* are known representatives of traditional Chinese medicine (TCM) and have been described for numerous indications.

Moreover, plant geni and species exist, such as *Armoracia rusticana, Capsicum* sp., *Cistus incanus, Echinacea angustifolia, Echinacea purpurea, Galphimia glauca, Melia toosendan, Olea europaea, Pelargonium* sp., *Phytolacca americana, Salix* sp., *Vitex agnus castus*, and *Vitis vinifera*, which are each considered to have pharmaceutical drug effects in the different indications.

Infection-relevant pathogenic agents exist, such as *Staphylococcus aureus, Staphylococcus epidermidis, Streptococcus pyogenes, Streptococcus pneumoniae* or *Haemophilus influenzae*. Among them is also a *Staphylococcus aureas* strain that is resistant to methicillin, called MRSA. Standard antibiotics such as beta-lactam antibiotics, for example oxacillin, penicillin and amoxicillin, increasingly no longer have an effect on this bacterium, because the excessive use of antibiotics, which do not fully destroy the pathogenic agents, have created resistivity. These germs represent an additional risk notably in surgical intensive care units ("point of care" areas), where they can cause pneumonia, wound infections, and blood poisoning or other life-threatening infections.

Therefore a high need exists to provide novel, effective, antibacterial agents for the treatment and for the prophylaxis of infections diseases.

It is therefore the object of the present invention to provide an agent that exhibits improved antibacterial efficacy.

Surprisingly, however, hydrolyzates of extracts of at least one plant drug from the respective geni, in particular the species of
*Equiseti herba* (horsetail herb), *Juglandis folium* (walnut leaf), *Millefolii herba* (yarrow), *Quercus cortex* (oak bark),

*Taraxaci herba* (dandelion herb), *Althaeae radix* (marshmallow root), and *Matricariae flos* (or *Flos chamomillae* (chamomile flower)), *Centaurium erythraea* (centaury), *Levisticum officinale* (lovage), *Rosmarinus officinalis* (rosemary), *Angelica dahurica* (Dahurian *angelica* root, Pinyin name: Bai Zhi), *Angelica sinensis* (Chinese *angelica*, Pinyin name: Dong quai), *Artemisia scoparia* (redstem wormwood, Pinyin name: Yin-chen), *Astragalus membranaceus* (var. *Mongolicus*) (Chinese milkvetch, Chin.: Huang Qi), *Leonurus japonicus* (Chinese motherwort, Chin.: Yimucao), *Salvia miltiorrhiza* (red sage, Chin.: Danshen), *Saposhnikovia divaricata* (siler, Pinyin name: Fang-feng), *Scutellaria baicalensis* (Baikal skullcap, Banzhilian), *Siegesbeckia pubescens* (*Siegesbeckia* herb, Pinyin name: Xi Xian Cao), *Armoracia rusticana* (horseradish), *Capsicum* sp. (peppers), *Cistus incanus* (hairy rockrose), *Echinacea angustifolia* (blacksamson echinacea), *Echinacea purpurea* (purple coneflower), *Galphimia glauca, Hedera helix* (English ivy), *Melia toosendan* (chinaberry fruit, Chin.: Chuan Lian Zi), *Olea europaea* (olive), *Pelargonium* sp. (geranium), *Phytolacca americana* (American pokeweed), *Primula veris* (cowslip), *Salix* sp. (willow), *Thymus* L. (thyme), *Vitex agnus castus* (lilac chastetree), and *Vitis vinifera* (common grape vine) exhibit an improved effect.

The invention relates in particular to a hydrolyzate comprising at least one extract, which is produced by extraction from dried plant material of:

a.) at least one of the plants, selected from the group consisting of:

the respective geni, notably the species of *Equiseti herba* (horsetail herb), *Juglandis folium* (walnut leaf), *Millefolii herba* (yarrow), *Quercus cortex* (oak bark), *Taraxaci herba* (dandelion herb), *Althaeae radix* (marshmallow root), and *Matricariae flos* (or *Flos chamomillae* (chamomile flower)), *Centaurium erythraea* (centaury), *Levisticum officinale* (lovage), *Rosmarinus officinalis* (rosemary), *Angelica dahurica* (Dahurican *angelica* root, Pinyin name: Bai Zhi), *Angelica sinensis* (Chinese *angelica*, Pinyin name: Dong quai), *Artemisia scoparia* (redstem wormwood, Pinyin name: Yin-chen), *Astragalus membranaceus* (var. *Mongolicus*) (Chinese milkvetch, Chin.: Huang Qi), *Leonurus japonicus* (Chinese motherwort, Chin.: Yimucao), *Salvia miltiorrhiza* (red sage, Chin.: Danshen), *Saposhnikovia divaricata* (siler, Pinyin name: Fang-feng), *Scutellaria baicalensis* (Baikal skullcap, Banzhilian), *Siegesbeckia pubescens* (*Siegesbeckia* herb, Pinyin name: Xi Xian Cao), *Armoracia rusticana* (horseradish), *Capsicum* sp. (peppers), *Cistus incanus* (hairy rockrose), *Echinacea angustifolia* (blacksamson echinacea), *Echinacea purpurea* (purple coneflower), *Galphimia glauca, Hedera helix* (English ivy), *Melia toosendan* (chinaberry fruit, Chin.: Chuan Lian Zi), *Olea europaea* (olive), *Pelargonium* sp. (geranium), *Phytolacca americana* (American pokeweed), *Primula veris* (cowslip), *Salix* sp. (willow), *Thymus* L. (thyme), *Vitex agnus castus* (lilac chastetree), and *Vitis vinifera* (common grape vine);

and a mixture or sub-combination thereof,
wherein the hydrolyzate can be obtained from the extract by way of hydrolytic treatment using a mineral acid, optionally removing the extracting agent.

A preferred combination is *Centaurium erythraea* (centaury), *Levisticum officinale* (lovage) and *Rosmarinus officinalis* (rosemary).

A further preferred combination comprises *Equiseti herba* (horsetail herb), *Juglandis folium* (walnut leaf), *Millefolii herba* (yarrow), *Quercus cortex* (oak bark), *Taraxaci herba* (dandelion herb), *Althaeae radix* (marshmallow root), and *Matricarias flos* (or *Flos chamomillae* (chamomile flower)).

A preferred combination comprises *Thymus* L. (thyme), *Primula veris* (cowslip) and/or *Hedera helix* (English ivy).

Furthermore, *Echinacea purpurea* herb and root are preferred. Moreover, *Primula veris* flowers and root are preferred.

The plants (plant drugs) according to the invention can be obtained, as is customary for the respective plant drug, from preferred parts of the plants, such as leaves, roots and the like.

A preferred hydrolyzate is characterized in that the extracts can be produced from the plant material using an extracting agent comprising 40 to 60% by volume, and more particularly 50% by volume ethanol and 40 to 60% by volume, and more particularly 50% by volume water over 24 hours while stirring and subsequent vacuum evaporation of the solvent.

A further preferred embodiment of the invention is a hydrolyzate which can be obtained by the hydrolytic treatment of the plant extracts with hydrochloric acid as the mineral acid, and more particularly hydrochloric acid having a concentration of 1 M to 10 M, preferably 6 to 9 M, and more particularly approximately 8 M, at 80° C. to 100° C., more particularly approximately 90° C., for 30 minutes to 120 minutes, in particular 40 minutes to 60 minutes, preferably approximately 45 minutes. In the final solution, the concentration of the hydrochloric acid is preferably 1 to 4 M, in particular 1 to 2 M, and more particularly 1.3 M.

It is preferred to carry out the hydrolytic treatment of the extracts in the presence of ethanol, and more preferably ethanol diluted with water, preferably 50% by volume ethanol.

The mixing of the extracts with the mineral acid can be carried out after removing the extracting agent or with the extracting agent.

Within the context of the present invention, the term "hydrolyzate" denotes an aqueous phase obtained from the extract of the plant (drug) according to the invention, in which the hydrolysis products are enriched. The hydrolysis preferably takes place under the action of acid, such as hydrochloric acid, phosphoric acid, sulfuric acid, mineral acid, and more particularly diluted mineral acid. The extract can be obtained, for example, by means of an aqueous-ethanolic extraction from a plant (drug), mixed by means of aqueous acid, evaporated to dryness, and subsequently received in water. The hydrolysis causes the chemical splitting of ingredients, wherein formally hydrogen and hydroxide are added to the respective cleavage product. The hydrolysis brings about a change in the substance composition of the hydrolyzate as compared to the existing known aqueous-ethanolic extracts.

In order to ensure that the hydrolyzates of the present invention have good physiological compatibility, the extracts are evaporated to dryness after the acid treatment step, received preferably in water, a buffer, or in diluted ethanol, and optionally neutralized with a pharmaceutically acceptable alkali. Possible alkalis are, for example, NaOH, $Na_2CO_3$ or $Na_2HPO_4$, without being exhaustive.

It came as a complete surprise when it was found that the hydrolyzates according to the invention exhibit an antibacterial effect.

The hydrolyzates of the present invention generally exhibit a significant antibacterial effect, which in the therapeutic range thereof is comparable to an antibiotic control agent comprising amoxicillin and clavulanic acid (mass ratio of 6:1).

The hydrolyzates of the present invention can be used to produce agents having an antibacterial effect against infection-relevant bacteria, in particular gram positive *cocci*, more particularly *Staphylococcus aureus, Staphylococcus epider-* midis, *Streptococcus pyogenes, Streptococcus pneumoniae, Streptococcus mutans* and/or gram negative rod bacteria, in particular *Haemophilus influenzae* and/or MRSA (methicillin-resistant *Staphylococcus aureus*).

The hydrolyzates were tested within the context of the present invention against the following ENT and respiratory tract relevant pathogenic agents and found to be effective against: *Staphylococcus aureus* (ATCC 25923), *Staphylococcus epidermidis* (ATCC 12228), *Streptococcus pneumoniae* (DSMZ 20566), *Streptococcus pyogenes* (DSMZ 20565), *Streptococcus mutans* (ATCC 35668), *Haemophilus influenzae* (DSMZ 4690), *Klebsiella pneumoniae* (ATCC 13883), and *Enterococcus casseliflavus* (VRE) (DSMZ 20680) as well as against the intestinal bacteria *Escherichia coli* (ATCC 25922), *Enterococcus faecalis* (VRE) (ATCC 19433), and *Pseudonomas aeruginosa*.

The hydrolyzates of the present invention can advantageously, and in manners which are known, be used to produce an antibacterial agent. Such antibacterial agents can be used for the protection against and/or treatment of infections, preferably orally or topically on the skin and mucous membranes, palate in the form of a pharmaceutical formulation that is in keeping with the applications thereof.

The pharmaceutical formulations of the hydrolyzates or antibacterial agents of the present invention are characterized in that the oral formulations comprise sugar-coated tablets, tablets, film-coated tablets, powders, capsules, or liquid dilutions, in particular drops, juices or syrups.

When used for topical applications, in particular sprays, ointments, emulsions, powders, ground substances, liquid or solid preparations for inhalation, compresses, wound and gum dressings, tamponades, tonsil brush solutions, gargling solutions, or rinsing solutions for the nose and ears are suited. The tamponades mentioned above are also suited for dental applications.

In order to use the hydrolyzates according to the invention as rinsing solutions for the nose and ears, these are advantageously used in combination with physiological or hyperosmolar concentrations of salts or salt mixtures. For the use as an antibacterial agent, it has been found that a preparation present as a lyophilizate has many advantages, these being in particular storage and long-term stability. The antibacterial agents of the present invention can, of course, contain the pharmaceutically customary adjuvants.

During microbiological analyses conducted at the Institute for Hygiene at the Medical University of Innsbruck, it was surprisingly found that the hydrolyzates according to the invention have a broad, in part pronounced antibacterial effect against skin, respiratory tract and ENT relevant pathogenic agents, which in corresponding tests with respect to the antibacterial effect were considerably more pronounced than was the case of non-hydrolyzed extracts. For example, antibacterial sensitivity tests using the agar diffusion test according to Mueller-Hinton (Mueller, H. J. and Hinton, J. (1941): A protein-free medium for primary isolation of the Gonococcus and Meningococcus. Proc. Soc. Expt. Biol. Med.; 48:330-333) showed that out of the hydrolyzed individual drug extracts the hydrolyzates according to the invention were effective against multiple pathogenic agents, and that the plurality of non-hydrolyzed mixtures surprisingly exhibited practically no antibacterial effect against the bacteria reference panel tested in the agar diffusion test.

It is also essential that this respectively achieved antibacterial efficacy also improves palliative and curative effects of the plants (plant drugs) according to the invention, including in the respective combination.

The hydrolyzates and the antibacterial agent of the present invention can therefore advantageously be used for the treatment of infections triggered by pathogenic agents. The optionally only anti-inflammatory effect of the analyzed drugs and drug mixtures is supplemented by the additional antibacterial effect, whereby an infection of the respiratory tracts is eliminated by destroying the bacterial pathogenic agents. Due to the medicinal effect based on at least one of the selected medicinal plants, a patient suffering from an infection will receive gentle treatment without synthetic-chemical components. In addition, the preparations according to the invention are marked by good compatibility with respect to the interactions thereof with other drugs and with respect to side effects, which rarely occur. The antibacterial agent of the present invention is effective in particular against the following pathogenic agents, exhibiting antibacterial efficacy in particular against gram positive *cocci* such as *Staphylococcus aureus, Staphylococcus epidermidis, Streptococcus pyogenes, Streptococcus pneumoniae*, and against gram negative rod-shaped bacteria such as *Klebsiella, Haemophilus influenzae, Pseudomonas aeruginosa* as well as against Enterobacteriaceae faecalis (VRE), Enterobacteriaceae casseliflavus and *E. coli*. As a result, the present invention also relates to the use of the hydrolyzates and antibacterial agents according to the invention for producing a pharmaceutical product for the treatment of infections, in particular infections of the respiratory tract and ENT space triggered by respiratory tract and ENT-relevant pathogenic agents.

In a further embodiment, the invention relates to a method for producing hydrolyzates, which can be obtained from at least one aqueous-ethanolic extract of at least one plant (drug) according to the invention, wherein preferably an aqueous-ethanolic extract is mixed with aqueous acid and subsequently the dissolved fractions are collected (=hydrolyzate).

The invention further relates to a method for producing an antibacterial agent, wherein in a first step a preferably aqueous-ethanolic extract is produced from at least one plant (drug) according to the invention and, in a second step, the extract that is obtained is mixed with an aqueous acid and the aqueous fractions are collected and optionally dried.

In a further embodiment of the invention, the hydrolyzates obtained can be converted into a dry mass. In a preferred embodiment, lyophilization of the hydrolyzates is carried out. However, other drying methods may also be employed.

Both the hydrolyzates according to the invention and the aqueous suspensions or dry masses thereof exhibit an antibacterial effect. The invention therefore relates to a corresponding antibacterial agent or to the use of the hydrolyzates according to the invention as an antibacterial agent.

The invention likewise relates to a pharmaceutical product, comprising a hydrolyzate of the plants (plant drugs) according to the invention, as described above, or a dry mass, or an antibacterial agent according to the invention for treating infections, more particularly respiratory tract infections, or to the use of the antibacterial agents according to the invention as a pharmaceutical product.

The term "infection" comprises all diseases, which cause a bacterial infectious disease as a result of the invasive incidence of bacteria in or on the human body or mammal. The development of an infectious diseases is significantly determined by the infectious (ability to transmit or contagiousness, ability to adhere or tenacity, ability to penetrate or invasiveness, ability to multiply or vitality) and pathogenic properties of the bacterium (pathogenicity). A distinction is made as follows: a) parenteral: percutaneous (through the skin), permucous (via the mucous membranes), inhalation infection; b) enteral (through the intestine); c) through a wound; d) directly from person or mammal to person or mammal, for example as a droplet infection, contact infection, dust infection; e) indirectly via intermediate carriers or intermediate hosts (vectors), such as an infectious chain; with courses as described in a) foudroyant (fast onset, very severe course, often fatal); b) acute (sudden onset, feverish course for days); c) chronic (gradual onset, subfebrile course for weeks, months or years); d) recurrent (occurring repeatedly, typically with acutely progressing fever-like relapses of the disease); e) latent (clinically silent phases over months or years). The pharmaceutical products according to the invention are suited for all types of infections mentioned.

The term "respiratory tract infections" comprises all forms of inflammation and/or infections of the respiratory tract caused by bacteria, notably tonsillitis, sinusitis and rhinitis. "Respiratory tracts" denotes the respiratory tract up to the alveoli; the upper respiratory tract comprises the sinus with the paranasal sinuses and the pharynx, where the air passage and the food passage cross. The lower respiratory tract begins with the larynx and follows the windpipe, including the entire branching of the bronchial tree.

The invention further relates to a pharmaceutical formulation containing a pharmaceutical product or antibacterial agent according to the invention. The antibacterial agents can be prepared in the form of pharmaceutical preparations in dosing units. This means that the preparation is present in the form of individual parts, for example tables, sugar-coated tablets, capsules, pills, suppositories and ampoules, the active ingredient content of which corresponds to a fraction or a multiple of a single dosage. The dosage units may contain, for example, 1, 2, 3 or 4 single doses or ½, ⅓ or ¼ of a single dose. A single dose preferably contains the amount of active ingredient that is administered with one application and usually corresponds to an entire, a half, a third or a quarter of a daily dose.

Non-toxic, inert pharmaceutically suitable excipients include solid, semisolid or liquid diluents, fillers and formulation adjuvants of all types.

Preferred pharmaceutical formulations that should be mentioned include in liquid form acid, aqueous, aqueous-acid, aqueous-organic, aqueous-acid-organic, aqueous-alcoholic, aqueous-acid-alcoholic or organic formulations, further tablets, sugar-coated tablets, capsules, pills, granules, suppositories, solutions, juice, suspensions and emulsions, pastes, ointments, gels, creams, lotions, powders and (nasal) sprays. Tablets, sugar-coated tablets, capsules, pills and granules may contain the active ingredient or active ingredients in addition to the customary excipients, such as a) fillers and extenders, for example starches, lactose, sucrose, glucose, mannitol, and silicic acid, b) binders, for example carboxymethyl cellulose, alginates, gelatin, polyvinylpyrrolidone, c) humectants, for example glycerin, d) disintegrating agents, for example agar-agar, calcium carbonate and sodium carbonate, e) dissolution retardants, for example paraffin, and f) resorption accelerating agents, for example quaternary ammonium compounds, g) wetting agents, for example cetyl alcohol, glycerol monostearate, h) adsorption agents, for example kaolin and bentonite, and i) lubricants, for example talcum, calcium stearate and magnesium stearate, and solid polyethylene glycols or mixtures of the substances listed in a) to i).

The tablets, sugar-coated tablets, capsules, pills, and granules can be provided with the customary coatings and encapsulations, optionally containing opaquing agents, and can also be composed so that they release, optionally with delay, the active ingredient or active ingredients only or preferably in a defined part of the intestinal tract, wherein polymer substances and waxes can be used, for example, as potting compounds.

The active ingredient or the active ingredients can optionally also be present with one or more of the excipients mentioned above in microencapsulated form.

In addition to the active ingredient or active ingredients, suppositories may contain the customary water-soluble or water-insoluble excipients, for example polyethylene glycols, fats, for example cocoa fat and higher esters (for example, C14-alcohol with C16-fatty acid) or mixtures of these substances.

In addition to the active ingredient or active ingredients, ointments, pastes, creams and gels may contain the customary excipients, for example animal and vegetable fats, waxes, paraffins, starch, tragant or cellulose derivatives, polyethylene glycols, silicones, bentonites, silicic acid, talcum, and zinc oxide, or mixtures of these substances.

In addition to the active ingredient or active ingredients, powders and sprays may contain the customary excipients, for example lactose, talcum, silicic acid, aluminum hydroxide, calcium silicate, and polymide powder, or mixtures of these substances. Sprays may additionally contain the customary propellants.

In addition to the active ingredient or active ingredients, solutions and emulsions may contain the customary excipients such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethyl formamide, oils, in particular cottonseed oil, peanut oil, corn oil, olive oil, castor oil and sesame oil, glycerin, glycerinformal, tetrahydrofurfuryl alcohol, polyethylene glycols and fatty acid esters of sorbitan, or mixtures of these substances.

In addition to the active ingredient or active ingredients, suspensions may contain customary excipients such as liquid diluents, for example water, ethyl alcohol, propylene glycol, suspending agents, for example ethoxylated isostearyl alcohols, polyoxyethylene sorbit and sorbitan esters, microcrystalline cellulose, aluminum metahydroxide, bentonite, agar-agar and tragant, or mixtures of these substances. The forms of formulations mentioned may also contain colorants, preservatives and odor- and flavor-enhancing additives, for example peppermint oil and eucalyptus oil, and sweeteners, for example saccharin.

For producing the extracts according to the invention and the combinations thereof from the plants, reference is made to the technical teachings, which are the subject matter of EP 1368605B1 and EP 0753306B1.

Additional advantages and characteristics of the present invention will be apparent from the description of the embodiments. The following examples are provided to describe the invention, without limiting the invention to these examples.

EXAMPLES

Preparation of the Test Solutions

The individual drugs and mixed extracts having variable drug compositions were extracted in 50% EtOH/$H_2O$ (v/v, approximately 1 g plant material for 20 ml solvent) for 24 hours at room temperature while stirring. 1.6 ml extract were mixed with 320 µl 25% HCl (corresponds to 8.1 mol/l) and 80 µl 50% EtOH and hydrolyzed for 45 minutes at 90° C. For comparison purposes, in a second step, the hydrolysis was conducted with 1 ml extract under the same conditions, while adding 1 ml 25% HCl. After concentrating the extracts by evaporation, the residue was received in 1 ml sterile water and tested for the antibacterial effect thereof. Screening method: 80 μl of the test solution were placed on Müller Hinton agar plates, or Müller Hinton Agar plates with 5% sheep blood, which contained an unknown concentration of the bacteria to be tested and incubated for 24 hours at 37° C.

Spiral platter (SP): A bacteria colony was suspended in 5 ml CASO-Bouillon and incubated for 24 hours at 37° C. The supernatant was removed after centrifuging the sample, washed with 0.9% NaCl, and diluted to a concentration of $10^7$ cfu/ml (colony forming unit per milliliter). The test solutions were diluted 1:2, 1:20 and 1:200 and mixed with the bacteria suspension (for Pneumococcus and *H. influenzae*: 1:10, for the remaining pathogens 1:100). 0.9% NaCl was used for positive control purposes. The samples are plated with a Whitley Automatic Spiral Platter (WASP) after 0, 4 and 8 hours and incubated for 24 hours at 37° C.

Table 1, evaluation: "+"=antibacterial activity; "(+)"=low antibacterial activity, "Ø"=no activity

|  | *Equiseti* | | *Juglandis* | | *Millefolii* | | *Quercus* | | *Taraxaci* | | *Althaeae* | | *Matricariae* | |
| --- | --- | --- | --- | --- | --- | --- | --- | --- | --- | --- | --- | --- | --- | --- |
|  | Platte | SP | Platte | SP | Platte | SP | Platte | SP | Platte | SP | Platte | SP | Platte | SP |
| *Staph. aureus* | Ø | | (+) | | Ø | | + | | Ø | | Ø | | Ø | |
| *P. aereginosa* | Ø | | (+) | | Ø | | + | | Ø | | Ø | | Ø | |
| *Pneumococcuss* | + | | Ø | | Ø | | Ø | | Ø | | Ø | | Ø | |
| *Streptococcus pyogenes* | Ø | | + | | Ø | | + | | Ø | | Ø | | Ø | |
| *Klebsiella* | Ø | | + | | Ø | | + | | Ø | | Ø | | Ø | |
| *E. coli* | Ø | | Ø | | Ø | | Ø | | Ø | | Ø | | Ø | |
| *H. influenzae* | Ø | | Ø | | Ø | | (+) | | Ø | | Ø | | Ø | |
| *Staph. epidermidis* | Ø | | + | | Ø | | + | | Ø | | Ø | | Ø | |
| *Ent. faecalis* (VRE) | Ø | | Ø | | Ø | | (+) | | Ø | | Ø | | Ø | |
| *Ent. casilliflavus* (VRE) | Ø | | Ø | | Ø | | Ø | | Ø | | Ø | | Ø | |

|  | *Althaeae hydrolysiert* | | *Equiseti hydrolysiert* | | *Taraxaci hydrolysiert* | | *Quercus hydrolysiert* | | *Matricariae hydrolysiert* | | *Millefolii hydrolysiert* | | *Junglandis hydrolysiert* | |
| --- | --- | --- | --- | --- | --- | --- | --- | --- | --- | --- | --- | --- | --- | --- |
|  | Platte | SP | Platte | SP | Platte | SP | Platte | SP | Platte | SP | Platte | SP | Platte | SP |
| *Staph. aureus* | Ø | | (+) | | Ø | | + | | Ø | | (+) | | Ø | |
| *P. aeroginosa* | Ø | | (+) | | Ø | | + | | (+) | | (+) | | Ø | |
| *Pneumococcus* | + | | + | | Ø | | (+) | | + | | + | | + | |
| *Streptcoccus pyogenes* | Ø | | Ø | | Ø | | + | | (+) | | (+) | | Ø | |
| *Klebsiella* | Ø | | (+) | | Ø | | (+) | | Ø | | Ø | | Ø | |
| *E. coli* | Ø | | (+) | | Ø | | (+) | | Ø | | Ø | | Ø | |
| *H. influenzae* | + | | (+) | | Ø | | + | | (+) | | (+) | | Ø | |
| *Staph. epidermidis* | Ø | | (+) | | Ø | | + | | Ø | | (+) | | Ø | |
| *Ent. faecalis* (VRE) | Ø | | (+) | | Ø | | + | | Ø | | (+) | | Ø | |
| *Ent. casilliflavus* (VRE) | Ø | | (+) | | Ø | | (+) | | (+) | | Ø | | Ø | |

Table 2, evaluation: "+"=antibacterial activity; "(+)"=low antibacterial activity, "Ø"=no activity
Canephron Compound:

Results of the Antibacterial Activity

| Bacterial strains | *Centaurium erythraea* | | *Levisticum officianale* | | *Rosmarinus officinalis* | |
| --- | --- | --- | --- | --- | --- | --- |
|  | no hydrol. | hydrol. | no hydrol. | hydrol. | no hydrol. | hydrol. |
| *Staphylococcus aureus* | Ø | + | Ø | + | + | + |
| *Pseudomonas aeruginosa* | Ø | + | Ø | + | Ø | + |
| *Streptococcus pneumonia* | Ø | + | Ø | + | (+) | + |
| *Streptococcus pyogenes* | Ø | + | Ø | + | + | + |
| *Klebsiella pneumoniae* | Ø | + | Ø | + | (+) | (+) |
| *Eschericia coli* | Ø | (+) | Ø | + | Ø | Ø |
| *Haemophilus influenzae* | Ø | (+) | Ø | + | Ø | + |
| *Staphylococcus epidermidis* | Ø | Ø | Ø | + | + | + |
| *Enterococcus faecalis* (VRE) | Ø | Ø | Ø | (+) | + | + |
| *Enterococcus casseliflavus* (VRE) | Ø | (+) | Ø | + | + | + |

Table 3, evaluation: "+"=antibacterial activity; "(+)"=low antibacterial activity, "Ø"=no activity Results of the Antibacterial Activity

| Bacterial strains | Angelica dahurica no hydrol. | Angelica dahurica hydrol. | Angelica sinensis no hydrol. | Angelica sinensis hydrol. | Artemisia scoparia no hydrol. | Artemisia scoparia hydrol. |
|---|---|---|---|---|---|---|
| Staphylococcus aureus | Ø | + | Ø | + | Ø | Ø |
| Pseudomonas aeruginosa | Ø | + | Ø | + | Ø | + |
| Streptococcus pneumoniae | Ø | + | + | + | Ø | (+) |
| Streptococcus pyogenes | Ø | + | Ø | + | Ø | (+) |
| Klebsiella pneumoniae | Ø | + | Ø | + | Ø | Ø |
| Escherichia coli | Ø | + | Ø | + | Ø | Ø |
| Haemophilus influenzae | Ø | + | Ø | + | Ø | + |
| Staphylococcus epidermidis | Ø | + | Ø | + | Ø | Ø |
| Enterococcus faecalis (VRE) | Ø | + | Ø | (+) | Ø | Ø |
| Enterococcus casseliflavus (VRE) | Ø | + | Ø | + | Ø | Ø |

Results of the Antibacterial Activity

| Bacterial strains | Saposhnikovia divaricata no hydrol. | Saposhnikovia divaricata hydrol. | Scutellaria baicalensis no hydrol. | Scutellaria baicalensis hydrol. | Siegesbeckia pubescens no hydrol. | Siegesbeckia pubescens hydrol. |
|---|---|---|---|---|---|---|
| Staphylococcus aureus | Ø | + | Ø | + | Ø | (+) |
| Pseudomonas aeruginosa | Ø | + | Ø | Ø | Ø | + |
| Streptococcus pneumoniae | Ø | + | Ø | + | Ø | + |
| Streptococcus pyogenes | Ø | + | Ø | (+) | Ø | + |
| Klebsiella pneumoniae | Ø | + | Ø | (+) | Ø | + |
| Escherichia coli | Ø | + | Ø | (+) | Ø | (+) |
| Haemophilus influenzae | Ø | + | Ø | + | Ø | (+) |
| Staphylococcus epidermidis | Ø | + | Ø | Ø | Ø | (+) |
| Enterococcus faecalis (VRE) | Ø | + | Ø | (+) | Ø | (+) |
| Enterococcus casseliflavus (VRE) | Ø | + | Ø | Ø | Ø | (+) |

Table 4, evaluation: "+"=antibacterial activity; "(+)"=low antibacterial activity, "Ø"=no activity Results of the Antibacterial Activity

| Bacterial strains | Armoracia rusticana no hydrol. | Armoracia rusticana hydrol. | Capsicum sp. no hydrol. | Capsicum sp. hydrol. |
|---|---|---|---|---|
| Staphylococcus aureus | Ø | + | Ø | + |
| Pseudomonas aeruginosa | Ø | + | Ø | + |
| Streptococcus pneumonia | Ø | + | + | + |
| Streptococcus pyogenes | Ø | + | Ø | + |
| Klebsiella pneumoniae | Ø | + | Ø | + |
| Escherichia coli | Ø | + | Ø | + |
| Haemophilus influenzae | Ø | + | Ø | + |
| Staphylococcus epidermidis | Ø | + | Ø | + |
| Enterococcus faecalis (VRE) | Ø | + | Ø | + |
| Enterococcus casseliflavus (VRE) | Ø | + | Ø | + |

Results of the Antibacterial Activity

|  | Cistus incanus | | Ech. purpurea radix | | Ech. purpurea herba | |
|---|---|---|---|---|---|---|
| Bacterial strains | no hydrol. | hydrol. | no hydrol. | hydrol. | no hydrol. | hydrol. |
| Staphylococcus aureus | + | + | Ø | + | Ø | (+) |
| Pseudomonas aeruginosa | Ø | + | Ø | + | Ø | + |
| Streptococcus pneumoniae | (+) | + | Ø | + | Ø | + |
| Streptococcus pyogenes | (+) | + | Ø | + | Ø | + |
| Klebsiella pneumoniae | Ø | + | Ø | + | Ø | + |
| Escherichia coli | Ø | + | Ø | + | Ø | (+) |
| Haemophilus influenzae | Ø | + | Ø | + | Ø | (+) |
| Staphylococcus epidermidis | + | + | Ø | + | Ø | Ø |
| Enterococcus faecalis (VRE) | + | + | Ø | + | Ø | + |
| Enterococcus casseliflavus (VRE) | Ø | + | Ø | + | Ø | Ø |

Ech. = Echinacea

Results of the Antibacterial Activity

|  | Galphimia glauca | | Hedera helix | | Melia toosendan | |
|---|---|---|---|---|---|---|
| Bacterial strains | no hydrol. | hydrol. | no hydrol. | hydrol. | no hydrol. | hydrol. |
| Staphylococcus aureus | (+) | (+) | Ø | (+) | Ø | + |
| Pseudomonas aeruginosa | Ø | Ø | Ø | + | Ø | + |
| Streptococcus pneumoniae | Ø | + | (+) | + | + | + |
| Streptococcus pyogenes | (+) | + | + | (+) | Ø | + |
| Klebsiella pneumoniae | Ø | Ø | Ø | + | Ø | + |
| Escherichia coli | Ø | Ø | Ø | (+) | Ø | + |
| Haemophilus influenzae | Ø | (+) | + | (+) | Ø | + |
| Staphylococcus epidermidis | (+) | (+) | (+) | Ø | Ø | + |
| Enterococcus faecalis (VRE) | Ø | Ø | Ø | Ø | Ø | + |
| Enterococcus casseliflavus (VRE) | Ø | + | Ø | + | Ø | + |

Results of the Antibacterial Activity

|  | Olea europaea | | Pelargonium sp. | | Phytolacca americana | |
|---|---|---|---|---|---|---|
| Bacterial strains | no hydrol. | hydrol. | no hydrol. | hydrol. | no hydrol. | hydrol |
| Staphylococcus aureus | + | + | + | + | Ø | + |
| Pseudomonas aeruginosa | Ø | + | Ø | + | Ø | + |
| Streptococcus pneumoniae | Ø | + | Ø | + | Ø | Ø |
| Streptococcus pyogenes | Ø | + | + | + | Ø | Ø |
| Klebsiella pneumoniae | (+) | + | Ø | + | Ø | + |
| Escherichia coli | Ø | + | Ø | + | Ø | + |
| Haemophilus influenzae | Ø | + | Ø | + | Ø | Ø |
| Staphylococcus epidermidis | + | + | + | + | Ø | + |
| Enterococcus faecalis (VRE) | Ø | + | + | + | Ø | + |
| Enterococcus casseliflavus (VRE) | Ø | + | + | + | Ø | Ø |

Results of the Antibacterial Activity

|  | Primula varia radix | | Salix sp. | | Thymus L. | |
|---|---|---|---|---|---|---|
| Bacterial strains | no hydrol. | hydrol. | no hydrol. | hydrol. | no hydrol. | hydrol. |
| Staphylococcus aureus | + | + | + | + | + | + |
| Pseudomonas aeruginosa | Ø | + | + | + | Ø | + |

-continued

| Bacterial strains | Primula varia radix no hydrol. | Primula varia radix hydrol. | Salix sp. no hydrol. | Salix sp. hydrol. | Thymus L. no hydrol. | Thymus L. hydrol. |
|---|---|---|---|---|---|---|
| Streptococcus pneumoniae | + | + | + | + | Ø | + |
| Streptococcus pyogenes | + | + | + | + | + | + |
| Klebsiella pneumoniae | Ø | + | + | + | Ø | + |
| Escherichia coli | Ø | + | + | + | Ø | + |
| Haemophilus influenzae | (+) | + | + | (+) | Ø | (+) |
| Staphylococcus epidermirdis | (+) | Ø | + | + | Ø | + |
| Enterococcus faecalis (VRE) | (+) | (+) | + | + | Ø | + |
| Enterococcus casseliflavus (VRE) | Ø | (+) | + | + | Ø | + |

Results of the antibacterial activity

| Bacterial strains | Vitex agnus castus no hydrol. | Vitex agnus castus hydrol. | Vitis vinifera no hydrol. | Vitis vinifera hydrol. | Ech. angustifolia no hydrol. | Ech. angustifolia hydrol. |
|---|---|---|---|---|---|---|
| Staphylococcus aureus | Ø | + | + | + | Ø | + |
| Pseudomonas aeruginosa | Ø | + | Ø | + | Ø | + |
| Streptococcus pneumoniae | Ø | + | Ø | + | Ø | + |
| Streptococcus pyogenes | (+) | + | Ø | + | Ø | + |
| Klebsiella pneumoniae | Ø | + | Ø | + | Ø | + |
| Escherichia coli | Ø | (+) | Ø | + | Ø | + |
| Haemophilus influenzae | Ø | + | Ø | + | Ø | + |
| Staphylococcus epidermidis | Ø | (+) | Ø | + | Ø | + |
| Enterococcus faecalis (VRE) | Ø | + | Ø | + | Ø | + |
| Enterococcos casseliflavus (VRE) | Ø | (+) | Ø | + | Ø | + |

Disk diffusion assay of TCM drugs

| Bacterial strains | Huang qi no hydrol. | Huang qi hydrol. | Ch. motherwort no hydrol. | Ch. motherwort hydrol. | Red sage no hydrol. | Red sage hydrol. |
|---|---|---|---|---|---|---|
| Staphylococcus aureus | Ø | + | Ø | + | + | + |
| Pseudomonas aeruginosa | Ø | + | Ø | + | Ø | + |
| Streptococcus pneumoniae | Ø | + | (+) | + | + | + |
| Streptococcus pyogenes | Ø | + | + | + | (+) | + |
| Klebsiella pneumoniae | Ø | + | (+) | + | Ø | + |
| Escherichia coli | Ø | + | Ø | + | Ø | + |
| Haemophilus influenzae | Ø | + | Ø | + | Ø | + |
| Staphylococcus epidermidis | Ø | + | Ø | + | + | + |
| Enterococcus faecalis (VRE) | Ø | + | Ø | + | + | + |
| Enterococcus casseliflavus (VRE) | Ø | + | Ø | + | + | + |

Legende: Huang qi (*Astragalus membranaceus*), Chinese motherwort (*Leonurus japonicus*), Red sage (*Salvia miltiorrhiza*)

The invention claimed is:

1. A hydrolyzate comprising at least one extract, which is produced by extraction from dried plant material of:
   c.) *Centaurium erythraea, Levisticum officinale* and *Rosmarinus officinalis*; or
   d.) *Equiseti herba, Juglandis folium, Millefolii herba, Quercus cortex, Taraxaci herba, Althaeae radix*, and *Matricariae flos*; or
   e.) i) *Thymus L.*,
      ii) *Primula veris*,
      iii) *Thymus L.* and *Hedera helix*, or
      iv) *Primula veris* and *Hedera helix*;
   wherein the hydrolyzate is obtained from the extract by way of hydrolytic treatment using a mineral acid,
   wherein that the extracts are produced from the plant material using an extracting agent comprising 40 to 60% by volume ethanol and 40 to 60% by volume water over 6 hours to 36 hours, while stirring and optionally vacuum evaporation of the solvent.

2. The hydrolyzate according to claim 1, wherein that the extracts are produced from the plant material using an extracting agent over 12 to 30 hours, while stirring and optionally vacuum evaporation of the solvent.

3. The hydrolyzate according to claim 1, wherein the hydrolyzate is obtained by the hydrolytic treatment of the extracts with hydrochloric acid as the mineral acid, in a concentration of 1 M to 10 M, at 80° C. to 100° C., for 30 minutes to 120 minutes, and/or the final solution has a concentration of the hydrochloric acid of 1 to 4 M.

4. A hydrolyzate according to claim 1, wherein the hydrolyzate exhibits an antibacterial effect.

5. A hydrolyzate according to claim 4, wherein the antibacterial effect, as compared to the non-hydrolytically treated pure plant drugs, in terms of the therapeutic range thereof is comparable to an antibiotic control agent comprising amoxicillin and clavulanic acid in a mass ratio of 6:1.

6. A hydrolyzate according to claim 4, wherein the antibacterial effect is directed against skin, ears, nose and throat, and respiratory tract relevant bacteria.

7. A hydrolyzate according to claim 4, wherein the antibacterial effect is directed against *Staphylococcus aureus, Staphylococcus epidermidis, Streptococcus pyogenes, Streptococcus pneumoniae, Streptococcus mutans* and/or gram negative rod bacteria.

8. A hydrolyzate according to claim 4, wherein the antibacterial effect is directed against *Haemophilus influenzae* and/or methicillin-resistant *Staphylococcus aureus* (MSRA).

9. A hydrolyzate according to claim 1, wherein the hydrolyzate is present in the form of a dry mass or aqueous suspension, and optionally is present in neutralized form.

10. An antibacterial agent containing the hydrolyzate according to claim 1.

11. A pharmaceutical product comprising the antibacterial agent according to claim 10 for the treatment of infections.

12. A pharmaceutical product comprising the antibacterial agent according to claim 10 for the treatment of respiratory tract infections.

13. A pharmaceutical product comprising the antibacterial agent according to claim 10 for the treatment of tonsillitis, sinusitis, or rhinitis.

14. A pharmaceutical compound containing the hydrolyzate according to claim 1, in the form of powder, granules, a tablet, or in liquid form as acid, aqueous, aqueous-acid, aqueous-organic, aqueous-acid-organic, aqueous-alcoholic, aqueous-acid-alcoholic or organic formulations or a formulation for topical application or solid preparations for inhalation, compresses, wound and gum dressings, tamponades, tonsil brush solutions, gargling solutions or rinsing solutions for the nose and ears, or a lyophilizate.

15. The hydrolyzate according to claim 1, wherein the hydrolyzate is obtained by the hydrolytic treatment of the extracts with hydrochloric acid as the mineral acid, in a concentration of 6 to 9 M, at 80° C. to 100° C., for 40 minutes to 60 minutes, and/or the final solution has a concentration of the hydrochloric acid of 1 to 2 M.

16. A hydrolyzate according to claim 1, wherein the hydrolyzate is present in an oral formulation as sugar-coated tablets, film-coated tablets, capsules, liquid dilutions, sprays, ointments, emulsions, powder, ground material, liquid or solid preparations for inhalation, compresses, wound and gum dressings, tamponades, tonsil brush solutions, gargling solutions or rinsing solutions for the nose and ears, or a lyophilizate.

17. A hydrolyzate according to claim 1, wherein the hydrolyzate is present in an oral formulation as drops, juices or syrups.

18. A pharmaceutical compound containing the hydrolyzate according to claim 1, in the final of powder, granules, a tablet, or in liquid form as acid, aqueous, aqueous-acid, aqueous-organic, aqueous-acid-organic, aqueous-alcoholic, aqueous-acid-alcoholic or organic formulations, capsules, drops, juices, syrups, sprays, ointments, emulsions, powder, ground material, liquid or solid preparations for inhalation, compresses, wound and gum dressings, tamponades, tonsil brush solutions, gargling solutions or rinsing solutions for the nose and ears, or a lyophilizate.

19. The hydrolyzate according to claim 1, wherein the at least one extract is produced by extraction from dried plant material of *Centaurium erythraea, Levisticum officinale* and *Rosmarinus officinalis*.

20. The hydrolyzate according to claim 1, wherein the at least one extract is produced by extraction from dried plant material of *Equiseti herba, Juglandis folium, Millefolii herba, Quercus cortex, Taraxaci herba, Althaeae radix*, and *Matricariae flos*.

21. The hydrolyzate according to claim 1, wherein the at least one extract is produced by extraction from dried plant material of
   i) *Thymus* L.,
   ii) *Primula veris*,
   iii) *Thymus* L. and *Hedera helix*, or
   iv) *Primula veris* and *Hedera helix*.

22. A hydrolyzate comprising
   A) at least one extract, which is produced by extraction from dried plant material of:
      c.) *Centaurium erythraea, Levisticum officinale* and *Rosmarinus officinalis*; or
      d.) *Equiseti herba, Juglandis folium, Millefolii herba, Quercus cortex, Taraxaci herba, Althaeae radix*, and *Matricariae flos*; or
      e.) i) *Thymus* L.,
         ii) *Primula veris*,
         iii) *Thymus* L. and *Hedera helix*, or
         iv) *Primula veris* and *Hedera helix*;
   wherein the hydrolyzate is obtained from the extract by way of hydrolytic treatment using a mineral acid, and
   B) at least one extract, which is produced by extraction from dried plant material of:
   a.) at least one of the plants, selected from the group consisting of at least one genus: *Equiseti, Juglandis, Millefolii, Quercus, Taraxaci, Althaeae, Matricariae, Centaurium, Levisticum, Rosmarinus, Angelica(e), Artemisia, Astragalus, Leonurus, Salvia, Saposhnikovia, Scutellaria, Siegesbeckia, Armoracia, Capsicum, Cistus, Echinacea, Galphimia, Hedera, Melia, Olea, Pelargonium, Phytolacca, Primula, Salix, Thymus, Vitex*, or *Vitis*;
   and a mixture thereof; or
   b.) at least one of the plants, selected from the group consisting of at least one species:
   *Equiseti herba, Juglandis folium, Millefolii herba, Quercus cortex, Taraxaci herba, Althaeae radix, Matricariae flus, Centaurium erythraea, Levisticum officinale, Rosmarinus officinalis, Angelica dahurica, Angelica sinensis, Artemisia scoparia, Astragalus membranaceus* var. *Mongolicus, Leonurus japonicus, Salvia miltiorrhiza, Saposhnikovia divaricata, Scutellaria baicalensis, Siegesbeckia pubescens, Armoracia rusticana, Capsicum* sp., *Cistus incanus, Echinacea angustifolia, Echinacea purpurea, Galphimia glauca, Melia toosendan, Olea europaea, Pelargonium* sp., *Phytolacca americana, Primula veris, Salix* sp., *Thymus* L., *Vitex agnus castus*, and *Vitis vinifera*,
   wherein the hydrolyzate is obtained from the extract by way of hydrolytic treatment using a mineral acid, and
   wherein that the extracts are produced from the plant material using an extracting agent comprising 40 to 60% by volume ethanol and 40 to 60% by volume water over 6 hours to 36 hours, while stirring and optionally vacuum evaporation of the solvent.

* * * * *